(12) United States Patent
Zhu et al.

(10) Patent No.: US 12,090,254 B2
(45) Date of Patent: Sep. 17, 2024

(54) COMPOSITE TUBULAR MATERIAL PREPARED FROM EXTRACELLULAR MATRIX AND SYNTHETIC POLYMER, AND PREPARATION METHOD THEREOF

(71) Applicant: NANKAI UNIVERSITY, Tianjin (CN)

(72) Inventors: Meifeng Zhu, Tianjin (CN); Yueyue Yang, Tianjin (CN); Wen Li, Tianjin (CN); Deling Kong, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 18/115,511

(22) Filed: Feb. 28, 2023

(65) Prior Publication Data

US 2024/0024539 A1 Jan. 25, 2024

(30) Foreign Application Priority Data

Jul. 19, 2022 (CN) .......................... 202210845262.2

(51) Int. Cl.
*A61L 29/12* (2006.01)
*A61L 29/00* (2006.01)
*B29D 23/00* (2006.01)

(52) U.S. Cl.
CPC ............. *A61L 29/12* (2013.01); *A61L 29/005* (2013.01); *B29D 23/00* (2013.01)

(58) Field of Classification Search
CPC ........ A61L 29/12; A61L 19/005; B29D 23/00
See application file for complete search history.

(56) References Cited

FOREIGN PATENT DOCUMENTS

| CN | 102284083 A | | 12/2011 |
|---|---|---|---|
| CN | 106109054 A | | 11/2016 |
| CN | 110201223 A | * | 9/2018 |
| CN | 111973313 A | | 11/2020 |
| CN | 114225111 A | | 3/2022 |
| CN | 114470327 A | | 5/2022 |

* cited by examiner

*Primary Examiner* — Alma Pipic

(57) ABSTRACT

The present disclosure discloses a composite tubular material and a preparation method thereof. The tubular material is prepared from extracellular matrix and directionally arranged synthetic polymer fibers through compounding; the synthetic polymer fibers serve as an internal skeleton, a fiber diameter ranges from 1 μm to 2000 μm, a fiber angle ranges from 0° to 180°, and a wall thickness ranges from 1 μm to 1000 μm; and extracellular matrix components are obtained from human or animal tissue through decellularization. According to the present disclosure, the tubular material with bioactivity and excellent mechanical properties can be prepared from the synthetic polymer and the natural material extracellular matrix through compounding; the synthetic polymer fibers with controllable fiber angle and diameter serve as the internal skeleton of the tubular material, and accordingly the tubular material has the mechanical properties of resistance to bending and squeezing.

9 Claims, 7 Drawing Sheets

Stereoscopic observation

Cross section

Cross section

COMPOSITE TUBULAR MATERIAL PREPARED FROM EXTRACELLULAR MATRIX AND SYNTHETIC POLYMER, AND PREPARATION METHOD THEREOF

CROSS-REFERENCE TO RELATED APPLICATION

This application claims priority from the Chinese patent application 202210845262.2 filed Jul. 19, 2022, the content of which is incorporated herein in the entirety by reference.

TECHNICAL FIELD

The present disclosure belongs to the field of biomaterials, and particularly relates to a composite tubular material prepared from an extracellular matrix and synthetic polymer fibers, and a preparation method thereof.

BACKGROUND ART

Tubular tissue structures exist in systemic organ systems, such as a vascular system (arteries, veins and capillaries), a respiratory system (esophagus and trachea), a urinary system (ureters, urethra and bladder) and a gastrointestinal system. Remaining a tubular three-dimensional shape is one of the important factors for such tubular tissue to function. Similar to additional organ system tissue, the tubular tissue is susceptible to disease and dysfunction, which generally requires therapeutic intervention in the form of replacement with synthetic components, foreign tissue or autologous tissue. However, the function of a sampling part is easy to impair by autologous tissue sampling, and accordingly a second operation is required. A foreign tissue source is limited, a size is mismatched, and immune rejection also occurs. Although a synthetic polymer component is readily available, the biocompatibility is low, the regeneration potential is limited after in vivo implantation, and the long-term in vivo remodeling effect is poor. Natural materials, such as collagen and hyaluronic acids, are high in biocompatibility, but low in mechanical strength. Ideal tubular repair materials should have high biocompatibility, regeneration performance, matched mechanical properties, workability and the like while remaining a tubular three-dimensional structure. Extracellular matrix is an extracellular component of tissue which is most similar to natural tissue, and meanwhile can mediate a positive immune response. The effect thereof to promote tissue repair has been validated in a large number of studies and clinical practices. A customizable tubular material with appropriate mechanical strength and high biocompatibility can be prepared from the extracellular matrix and synthetic polymer materials through compounding, which is expected to solve the problems in current clinical treatment methods.

SUMMARY

In order to solve the problems in the prior art, the present disclosure provides a composite tubular material prepared from an extracellular matrix and synthetic polymer fibers, and a preparation method thereof to solve the problems of poor biocompatibility and limited regeneration potential of a tubular tissue repair material after in vivo implantation.

The technical solution of the present disclosure is as follows:

A composite tubular material prepared from extracellular matrix and synthetic polymer fibers is made from the extracellular matrix and directionally arranged synthetic polymer fibers through compounding; the synthetic polymer fibers serve as an internal skeleton, a diameter of the fiber ranges from 1 μm to 2000 μm, an angle of the fiber ranges from 0° to 180°, a tube wall thickness ranges from 1 μm to 1000 μm; and extracellular matrix components are obtained from human or animal tissue through decellularization.

The synthetic polymer is prepared from one or more of compounds of a polyglycolic acid, a poly(lactic-co-glycolic acid), polycaprolactone, a polylactic acid, poly(L-lactide-caprolactone), polyurethane, nylon, polyester, acrylic fibers, polyethylene glycol terephthalate, polypropylene, polyethylene, polycarbonate resin, polystyrene, poly(1,4-polyethylene succinate), poly(1,6-hexamethylene diisocyanate), poly(D-lactic acid), polyethylene glycol, polyglycolic acid, polyhydroxyalkanoate, poly(3-hydroxybutyrate), poly(3-hydroxybutyrate-co-3-hydroxyhexanoic acid), poly(3-hydroxybutyrate-co-3-hydroxyvaleric acid), poly(lactic acid-co-glycolide), poly(propylene fumarate) and poly(dihydroxypropyl fumarate).

A preparation method of a composite tubular material prepared from an extracellular matrix and synthetic polymer fibers, including the following steps:

step 1: preparation of an extracellular matrix solution; a specific method includes steps of selecting fresh tissue of animal origin, removing external fat, connective tissue and blood, and cutting the tissue into small segments or pieces; after disinfection and sterilization, repeatedly freeze-thawing the tissue, destructing cell membrane components through elution with Triton X-100, sodium deoxycholate or sodium dodecyl sulfate (SDS), then removing nucleic acid components through elution with DNase and RNase; grinding the tissue into powder after freeze drying, dissolving the powder in acid and stirring to obtain a uniform extracellular matrix solution with a mass/volume fraction ranging from 0.1% to 95%;

step 2: construction of a synthetic polymer fibrous skeleton; a specific method includes the step of processing synthetic polymers through melt spinning or wet spinning to prepare the fibrous skeleton; and step 3: preparation of a composite tubular material from the extracellular matrix solution and the fibrous skeleton through compounding; a specific method includes steps of soaking the fibrous skeleton into the extracellular matrix solution, and freeze-drying or repeatedly air-drying the fibrous skeleton after an extracellular matrix is filled into fiber pores; obtaining the tubular material with different compounding ratios of the extracellular matrix to the fibrous skeleton by regulating the concentration, filling time and frequency, and drying time of the extracellular matrix solution; cross-linking the tubular material with a cross-linking agent, and regulating the concentration and time of the cross-linking agent to complete cross-linking; and regulating pH to 6 to 8 to obtain the composite tubular material.

The method of preparing the fibrous skeleton through melt spinning in step 2 includes the following steps: installing receiving steel bars with different diameters as receivers on a melt spinning apparatus, adding the synthetic polymer to a constant temperature heating cylinder, heating to melt the polymer, then regulating a polymer fiber diameter, a fiber angle and a tube wall thickness by adjusting following parameters of a cylinder piston propulsion speed, an air pressure, a distance between a needle and the receiving bars, needle thickness, a revolving speed and a lateral movement speed of the receiving bars, and fiber receiving time, to prepare the synthetic polymer fibrous skeleton with a fiber diameter ranging from 1 μm to 1000 μm, a fiber angle ranging from 0° to 180°, and a tube wall thickness ranging from 1 μm to 3000 μm.

The method of preparing the fibrous skeleton through wet spinning in step 2 includes the following steps: installing steel bars with different diameters as receivers on a wet spinning apparatus, dissolving a synthetic polymer in a chemically pure reagent to prepare a solution with a mass/volume fraction ranging from 0.1% to 60%, filling the completely dissolved solution into a syringe, installing the syringe on a syringe pump, regulating a fiber diameter, a fiber angle and a tube wall thickness by regulating following parameters of a syringe pump propulsion speed, a needle thickness, a revolving speed and a movement speed of the receiving bars, and fiber receiving time, to prepare the fibrous polymer skeleton with a fiber diameter ranging from 1 μm to 1000 μm, a fiber angle ranging from 0° to 180°, and a tube wall thickness ranging from 1 μm to 3000 μm.

The cross-linking agent in step 3 includes one of glutaraldehyde, formaldehyde, EDC/NHS, genipin and quercetin.

A concentration of the extracellular matrix solution ranges from 0.1% to 95% (weight/volume), the filling time ranges from 0.1 hours to 72 hours, the frequency ranges from 1 time to 20 times, and the drying time ranges from 0.1 hours to 100 hours.

The parameter of the constant temperature heating cylinder is set to range from 40° C. to 400° C.

The parameter of the syringe pump is set to range from 0.1 ml/h to 100 ml/h.

The chemically pure reagent includes one of dichloromethane, trichloromethane, an acetic acid, acetone, trifluoroethanol and hexafluoroisopropanol.

Compared with reported tubular materials, the patent of the present disclosure has the following beneficial effects: 1. Most of tubular materials are prepared from synthetic polymers or natural polymer materials separately, and cannot meet the requirements for bioactivity and mechanical properties simultaneously; according to the present disclosure, the tubular material with bioactivity and excellent mechanical properties can be prepared from the synthetic polymer and the extracellular matrix of natural material through compounding; 2. For repair of a tubular tissue defect at a transarticular site, most of domestic and foreign tubular material products are lacking in unique design and consideration, and for the repair of blood vessels, nerves, and other tissue at this site, it is required that an implant product should be resistant to bending and squeezing during bending, and meanwhile keep in a stereoscopic pattern, to ensure tissue repair and regeneration. In the present disclosure, the synthetic polymer fibers with controllable fiber angle and diameter serve as the internal skeleton of the tubular material, and accordingly the tubular material has the function of resistance to bending and squeezing; 3. The preparation process of the tubular material is high in controllability, and the fiber diameter, angle and pore diameter of the fibrous polymer skeleton, the tube wall thickness and diameter of the tubular material and the like are adjustable. 4. The extracellular matrix of different tissue and synthetic polymer microfibers can be used for the repair of specific tubular tissue. 5. The tubular composite material prepared in the present disclosure can be used for repair and regeneration of different tubular tissue, such as blood vessels, veins, esophagi, tracheae, urethrae, ureters, lymphatic vessels, small intestines, lacrimal ducts and nerves.

BRIEF DESCRIPTION OF THE DRAWINGS

FIGS. 1A-1B show a stereomicroscope picture/MicroCT picture showing morphology of a composite tubular material/prepared from an extracellular matrix/polycaprolactone fibers; wherein FIG. 1A is a stereomicroscope picture showing morphology of a composite tubular material prepared from an extracellular matrix/polycaprolactone fibers; and FIG. 1B is a MicroCT picture showing a macrostructure of the composite tubular material prepared from the extracellular matrix/polycaprolactone fibers;

FIGS. 2A-2B are an SEM showing a microstructure of the tubular material prepared from the extracellular matrix/polycaprolactone fibers; wherein FIG. 2A is an overall diagram of the tubular material, and FIG. 2B is a partially enlarged view of FIG. 2A;

FIGS. 3A-3B are an H&E staining picture showing extracellular matrix components distributed among polycaprolactone fiber pores; wherein FIG. 3A is a sectional view of the tubular material, and FIG. 3B is a partially enlarged view of FIG. 3A.

DETAILED DESCRIPTION OF THE PRESENT DISCLOSURE

Figure 1A:
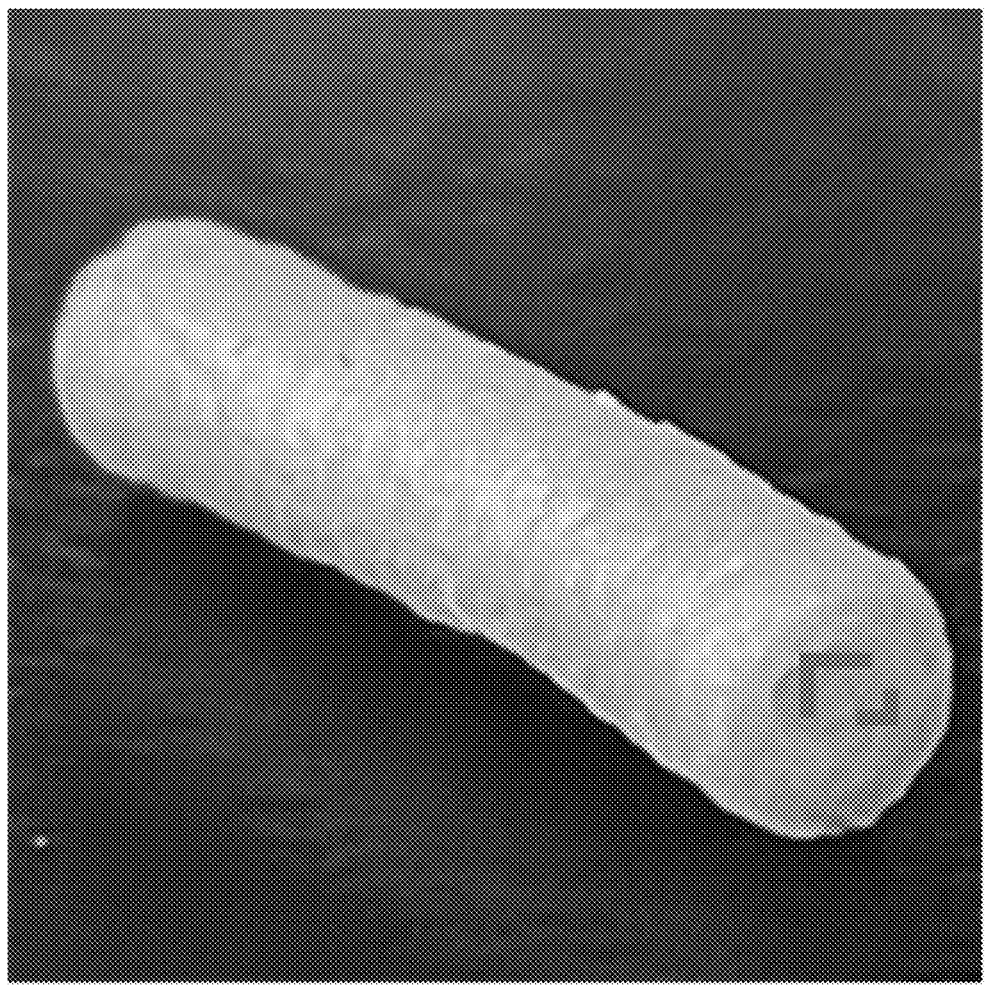

The technical solution of the present disclosure will be described below in detail with reference to accompanying drawings and embodiments.

Embodiment 1: Preparation of Composite Tubular Material from Nerve Extracellular Matrix/Polycaprolactone (PCL)

Preparation of a nerve extracellular matrix solution: fresh porcine sciatic nerve is taken, and cut into small segments after external fat, connective tissue and blood are removed; the sciatic nerve is completely frozen at −80° C., then completely unfrozen, and washed with sterile water, and such process is repeated for 5 times; the washed sciatic nerve is soaked in a mixed solution of 0.1% peroxyacetic acid and 4% ethyl alcohol, shaken at 100 rpm in a shaker for 2 hours, and washed with the sterile water; then the washed sciatic nerve is soaked in 3% (w/v) sterile Triton X-100, shaken and eluted at 100 rpm for 2 hours, the 3% (w/v) Triton X-100 is replaced with a new one, such process is repeated for 5 times, and the sciatic nerve is washed with the sterile water; the washed sciatic nerve is soaked in 4% (w/v) sterile sodium deoxycholate, shaken and eluted at 100 rpm for 2 hours, the 4% (w/v) sodium deoxycholate is replaced with a new one, such process is repeated for 5 times, and the sciatic nerve is washed with the sterile water, till there is no foam; a sterile mixed solution containing 6.25 U/mL of DNase, 1 U/mL of RNase, 55 mM of Tris-HCl (PH 6.4), 45 mM of $MgCl_2$ and mM of $CaCl_2$ is prepared, the sciatic nerve is shaken at 37° C. and 100 rpm and soaked for 12 hours, soaked in the sterile water, and washed at 100 rpm for 5 times, with each for 2 hours; and the washed sciatic nerve is ground into powder after being freeze-dried, and 0.3 g of powder is weighed and dissolved in 10 mL of 0.5 M acetic acid to obtain a 3% (w/v) n extracellular matrix solution, and the solution is stirred at room temperature for 12 hours to a homogeneous state.

Preparation of a PCL fibrous skeleton: a receiving bar with a diameter of 1.6 mm is installed on a melt spinning apparatus by a melt spinning method, 10 g of PCL is added to a constant temperature heating cylinder, heated to 75° C. and melted for 1 hour, a 19 G needle is selected, a distance between the needle and the receiving bar is set to 1 cm, pushing pressure is 6 barometric pressures, a revolving speed parameter of each receiving bar is 400 rpm, a movement speed parameter is 180 Hz, and receiving is stopped when the number of shifts is 50 rounds.

Preparation of a composite material from a nerve extracellular matrix and PCL fibers: the PCL fibrous skeleton is soaked in a 5% (m/v) acetic acid solution of 3% (w/v) nerve extracellular matrix, and rotationally air-dried in a sterile environment. The air-dried PCL fibrous skeleton is cross-linked with EDC (5 mg/mL)/NHS (1.5 mg/mL) (PH value is regulated to 8.0 with 1 M of $Na_2CO_3$ solution) at 4° C. for 2 hours, washed with the sterile water for 24 hours, and freeze-dried for 48 hours to obtain the composite material prepared from the nerve extracellular matrix and PCL.

Embodiment 2: Preparation of Composite Tubular Material from Decellularized Small Intestinal Submucosa/Polylactic Acid (PLA)

Preparation of a small intestinal submucosa extracellular matrix solution: a fresh porcine small intestine is taken and washed thoroughly, a mucous layer, a muscular layer, a serous membrane layer and lymph nodes of a porcine small intestine jejunum are scraped off mechanically, a submucosa is separated therefrom, cut into small segments, and washed till water is transparent; the submucosa is completely frozen at −80° C., then completely unfrozen, and washed with sterile water, such process is repeated for 3 times; the washed submucosa is soaked in a mixed solution of a 0.1% peroxyacetic acid and 4% ethyl alcohol, shaken and disinfected at 100 rpm for 2 hours, and washed with the sterile water; the washed submucosa is soaked in 1% (w/v) sterile SDS, shaken and eluted at 100 rpm for 2 hours, the 1% (w/v) SDS is replaced with a new one, such process is repeated for 3 times, and the submucosa is washed with the sterile water to remove the SDS; a sterile mixed solution containing 4.45 U/mL of DNase, 0.5 U/mL of RNase, 34 mM of Tris-HCl (PH6.4), 23 mM of $MgCl_2$ and 8 mM of $CaCl_2$) is prepared, the submucosa is shaken and soaked therein at 37° C. and 100 rpm for 12 hours; soaked in the sterile water, and washed at 100 rpm for 5 times, with each for 2 hours; and the washed submucosa is freeze-dried and ground into powder, and 0.15 g of the powder is weighed and dissolved in 10 mL of a 0.5 M acetic acid to obtain a 1.5% (w/v) SIS solution, and the solution is stirred at room temperature for 12 hours to a homogeneous state.

Preparation of a PLA fibrous skeleton: 1.5 g of PLA is weighed and added to 10 ml of hexafluoroisopropanol, the obtained mixture is dissolved overnight with stirring at room temperature, to obtain a PLA solution with a fraction concentration of 15% (w/v). The solution is sucked into a syringe installed on a syringe pump, a speed of the syringe pump is set to 2 mL/h, a syringe needle is arranged at the position 3 cm from an upper end of a receiving bar with a diameter of 3 mm in a spinning coagulation bath, a revolving speed of the receiving bar is set to 200 rpm, a movement speed is 120 Hz, receiving time is 40 minutes, and the coagulation bath and a spinning solution solvent are removed after completion.

Composite tubular material prepared from a small intestinal submucosa solution and a PLA fibrous skeleton: the PLA fibrous skeleton is soaked in a 1.5% (w/v) small intestinal submucosa extracellular matrix solution, vacuum pumping is conducted till there is no bubble in the solution, and the fibrous skeleton is rotationally air-dried in a sterile environment. The air-dried fibrous skeleton is cross-linked with EDC (4 mg/mL)/NHS (1 mg/mL) (PH value is regulated to 8.0 with 1 M of $Na_2CO_3$ solution) at the temperature of 4° C. for 2 hours, washed with the sterile water for 24 hours, and the solution is replaced once every 2 hours. The fibrous skeleton is freeze-dried to obtain the composite tubular material prepared from the small intestinal submucosa solution and the PLA fibrous skeleton.

Embodiment 3: Preparation of Composite Tubular Material from Vascular Extracellular Matrix/Polyurethane (PU)

Preparation of a vascular extracellular matrix solution: a fresh porcine aorta is taken and cut into small segments, completely frozen in liquid nitrogen, then unfrozen, and washed with sterile water, such process is repeated for 3 times; the aorta is soaked in a mixed solution of 0.3% peroxyacetic acid and 10% ethyl alcohol, shaken and disinfected at 100 rpm for 2 hours, and washed with the sterile water; the washed aorta is soaked in 1.5% (w/v) sterile Triton X-100, and shaken and eluted at 100 rpm for 2 hours, the 1.5% (w/v) Triton X-100 is replaced with new 2% (w/v) Triton X-100, such process is repeated for 4 times, and the aorta is washed with the sterile water to remove the Triton X-100; a sterile mixed solution containing 7 U/mL of DNase, 1.5 U/mL of RNase, 20 mM of Tris-HCl (PH 6.4), 30 mM of $MgCl_2$ and 8 mM of $CaCl_2$ is prepared, the washed aorta is shaken and soaked at 37° C. and 100 rpm for 12 hours to remove cell nuclei; the aorta is soaked in the sterile water, and washed at 100 rpm for 5 times, with each for 2 hours; and the washed the aorta is freeze-dried and ground into powder, and 0.6 g of powder is weighed and dissolved in 10 mL of 0.5 M acetic acid to obtain a 6% (w/v) s extracellular matrix solution, and the extracellular matrix solution is stirred at room temperature for 10 hours to a homogeneous state.

PLA fibrous skeleton: a receiving bar with a diameter of 6 mm is installed on a melt spinning apparatus by a melt spinning method, 10 g of PLA is added to a constant temperature heating cylinder, heated to 260° C. and melted for 1 hour, an 18 G needle is selected, a distance between the needle and the receiving bar is set to 0.5 cm, a pushing pressure is 4 barometric pressures, a revolving speed of the receiving bar is 100 rpm, a movement speed is 80 Hz, and receiving is stopped when a receiving movement frequency is 30.

Preparation of a tubular material from a vascular extracellular matrix/polyurethane (PU): the PLA fibrous skeleton is soaked in a 6% (w/v) s extracellular matrix solution, vacuum pumping is conducted till there is no bubble in the solution, and the fibrous skeleton is rotationally air-dried in a sterile environment. The air-dried fibrous skeleton is cross-linked with a 3% glutaraldehyde solution at 4° C. for 2 hours, and washed with the sterilized water for 24 hours, and the solution is replaced once every 2 hours. The fibrous skeleton is freeze-dried to obtain the tubular material prepared from the vascular extracellular matrix/polyurethane (PU).

Embodiment 4: Preparation of Composite Tubular Material from Lymphatic Extracellular Matrix/Poly(Lactic-Co-Glycolic Acid) (PLGA)

Preparation of a lymphatic extracellular matrix solution: a fresh porcine urethra is taken and cut into small segments, completely frozen in liquid nitrogen, then unfrozen, and washed with sterile water, and such process is repeated for 2 times; the washed urethra is soaked in a 75% ethanol solution, shaken and disinfected at 100 rpm for 30 minutes, and washed with the sterile water; the washed urethra is soaked in 1.5% (w/v) sterile SDS, and shaken and eluted at 300 rpm for 2 hours, new 1.0% (w/v) Triton X-100 is used, such process is repeated for 5 times, and the urethra is washed with the sterile water to remove the SDS and the Triton X-100; a sterile mixed solution containing 1 U/mL of DNase, 0.5 U/mL of RNase, 2 mM of Tris-HCl (PH6.4), 13 mM of $MgCl_2$ and 9 mM of $CaCl_2$) is prepared, the urethra is shaken and soaked at 37° C. and 500 rpm for 3 hours to remove cell nuclei; the urethra is soaked in the sterile water, washed at 400 rpm for 5 times, with each for 1 hour; the washed urethra is freeze-dried, and ground into powder, 0.7 g of powder is weighed and dissolved in 7 mL of 0.5 M acetic acid to obtain a 10% (w/v) s extracellular matrix solution, and the extracellular matrix solution is stirred at room temperature for 20 hours to a homogeneous state.

PLGA fibrous skeleton: a receiving bar with a diameter of 2 mm is installed on a melt spinning apparatus by a melt spinning method, 8 g of PLGA is added to a constant temperature heating cylinder, heated to 200° C. and melted for 1.5 hours, a 9 G needle is selected, a distance between the needle and the receiving bar is set to 1.5 cm, a pushing pressure is 1 barometric pressure, a revolving speed parameter of the receiving bar is 500 rpm, a movement speed parameter is 10 Hz, and receiving is stopped when the number of shifts is 50.

Preparation of a tubular material from a lymphatic extracellular matrix/PLGA: the PLGA fibrous skeleton is soaked in a 10% (w/v) s extracellular matrix solution, vacuum pumping is conducted till there is no bubble in the solution, and the fibrous skeleton is rotationally air-dried in a sterile environment. The air-dried fibrous skeleton is cross-linked with a 2% glutaraldehyde solution at 4° C. for 6 hours, and washed with the sterile water for 48 hours, and the solution is replaced once every 4 hours. The fibrous skeleton is freeze-dried to obtain the tubular material prepared from the lymphatic extracellular matrix/PLGA.

Figure 1B:
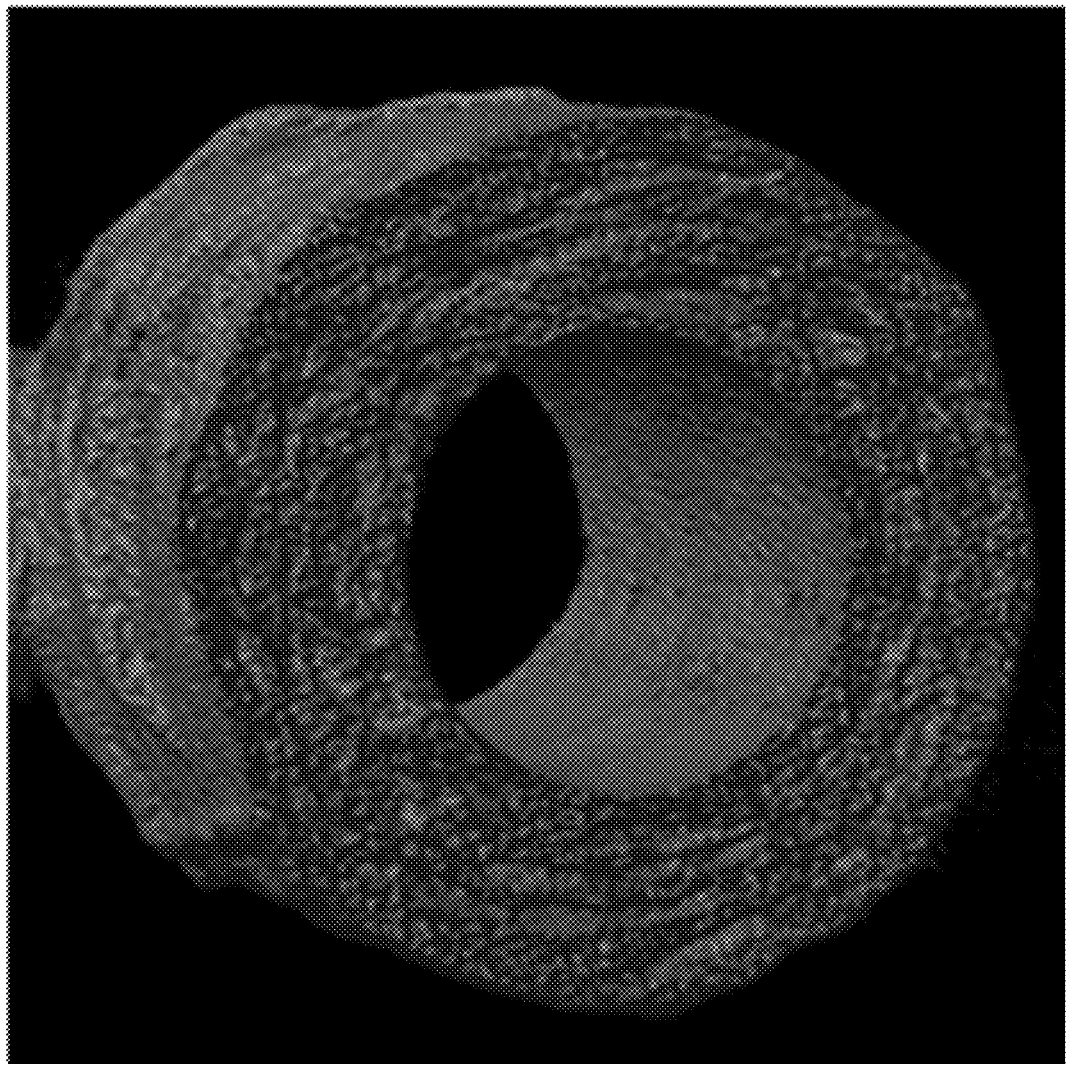
Figure 2A:
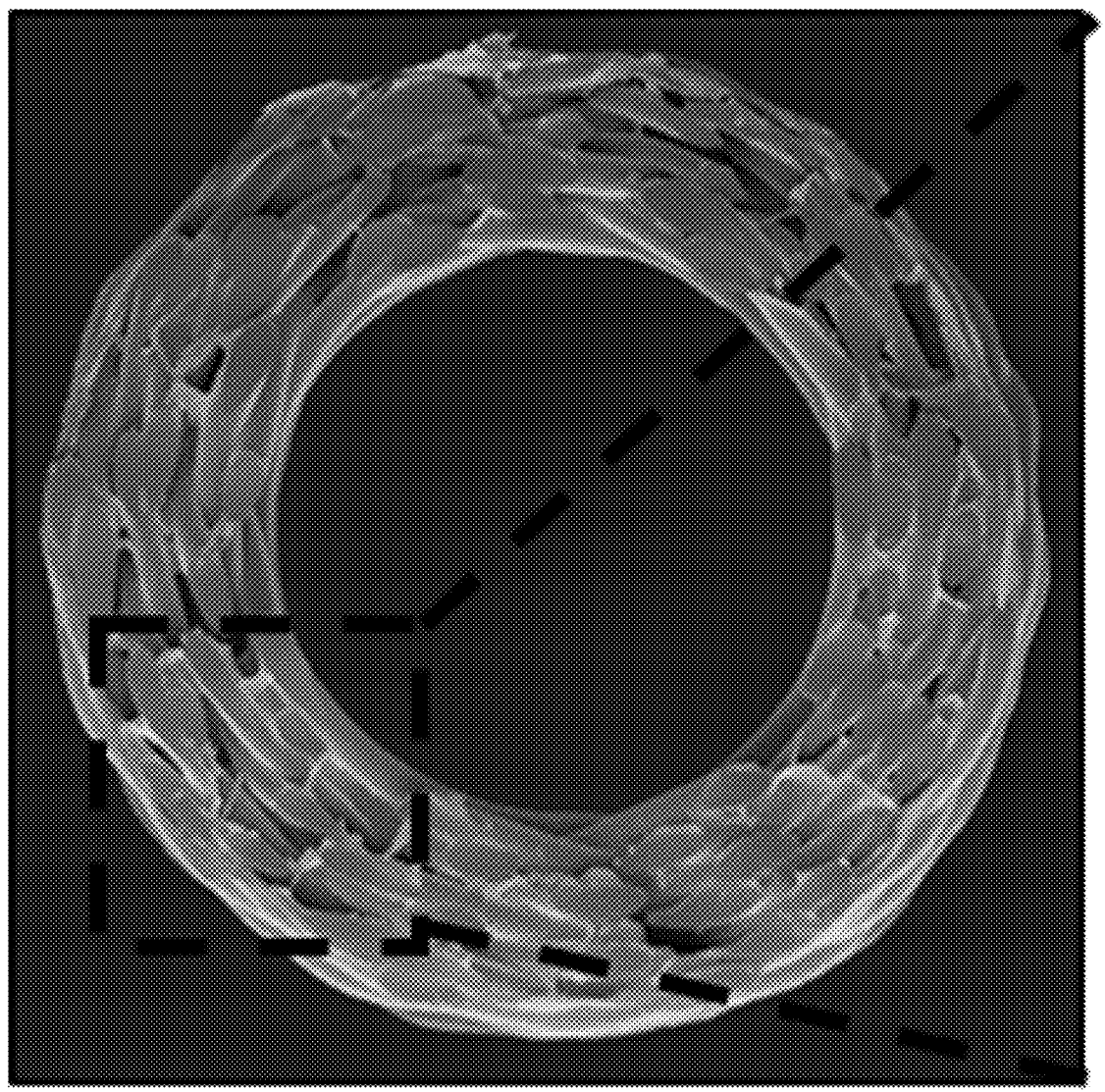
Figure 2B:
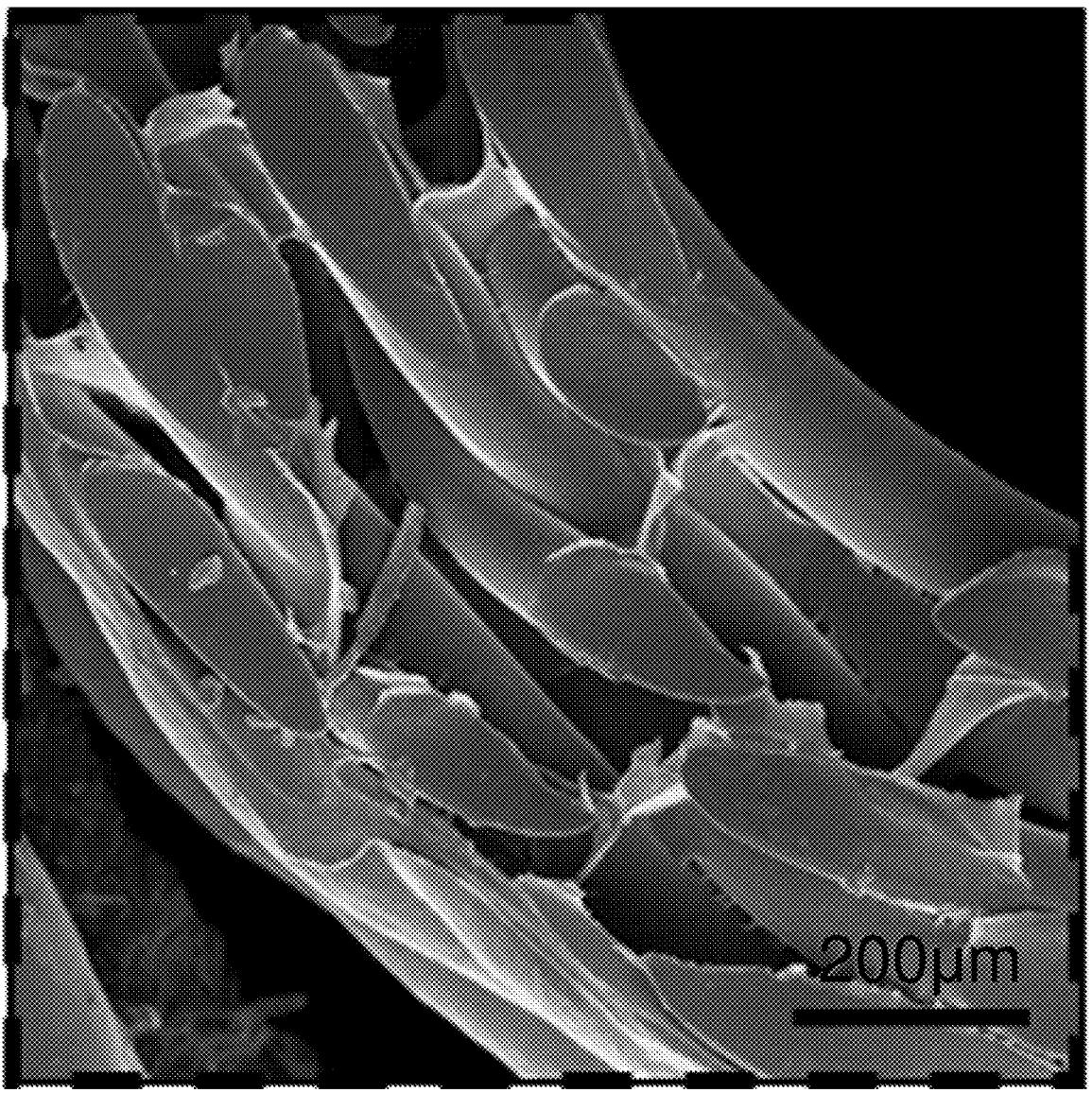
Figure 3A:
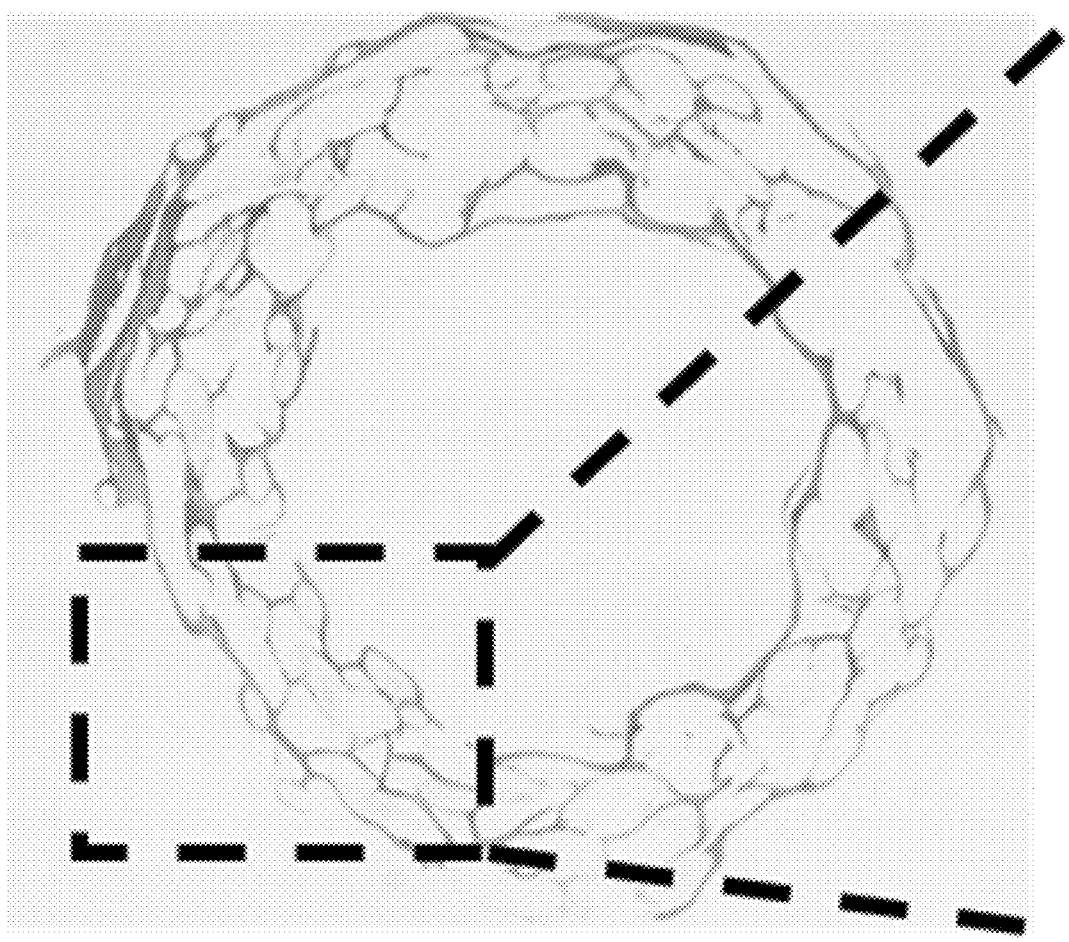
Figure 3B:
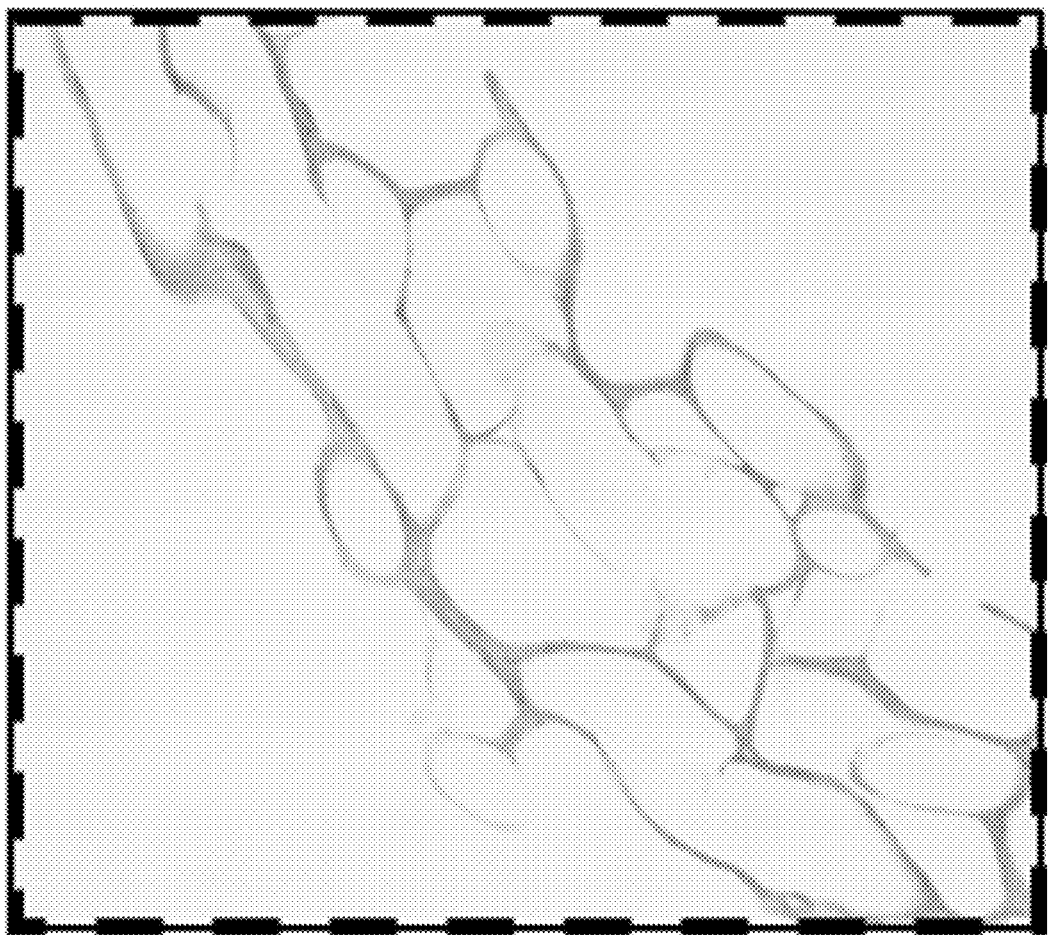
Figure 4:
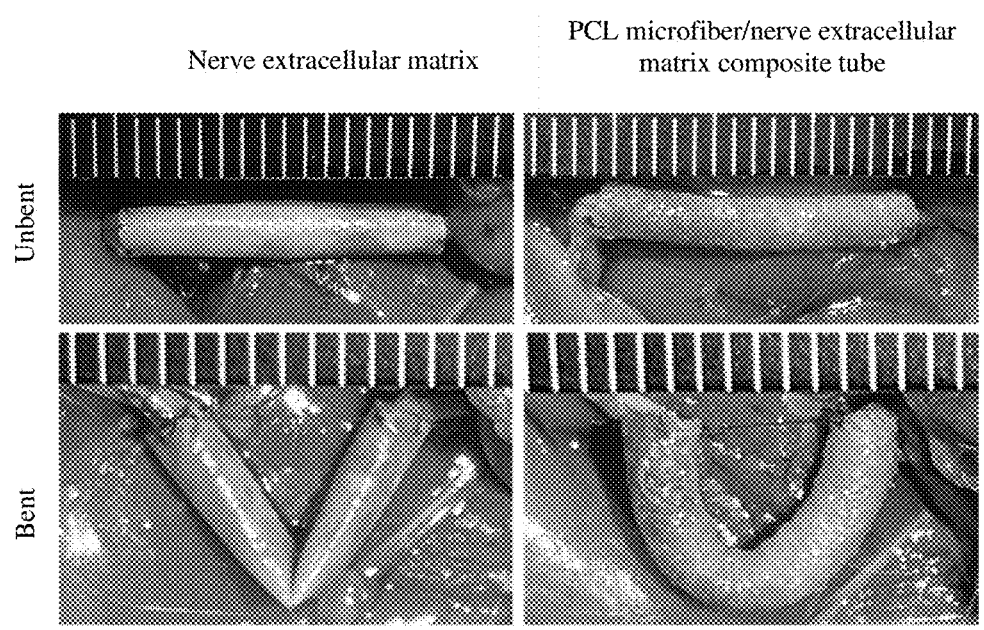
FIG. 4 illustrates a composite catheter with a length of 1.5 cm, which is implanted into a sciatic nerve defect site of a rat and bent by 180°, and does not form a dead fold.

The results show that the composite tubular material prepared from the PCL microfibers and the extracellular matrix is uniform in the tube wall structure and controllable in wall thickness and diameter (as shown in FIGS. 1A-1B), and the fibers have a uniform diameter and show circumferential surrounding (as shown in FIGS. 2A-2B). The extracellular matrix material may be distributed among the fibers uniformly (as shown in FIGS. 3A-3B). After the composite tubular material is implanted into the sciatic nerve defect site of the rat, and an extracellular matrix catheter is bent, a dead fold is formed, while a PCL microfiber/nerve extracellular matrix composite tube still keeps in a three-dimensional structure (as shown in FIG. 4).

What is claimed is:

1. A preparation method of a composite tubular material from an extracellular matrix and synthetic polymer fibers, comprising the following steps:
   step 1: preparing uniform extracellular matrix solution, comprising steps of selecting animal source tissue, removing external fat, connective tissue and blood, thus yielding a first process source tissue, and cutting the first process source tissue into segments or pieces; sterilizing and disinfecting the segments or pieces to obtain sterilized and disinfected segments or pieces, repeatedly freezing and thawing the sterilized and disinfected segments or pieces to yield a second process source tissue, destructing cell membrane components of the second process source tissue through elution with polyethylene glycol mono(4-tert-octylphenyl) ether, sodium deoxycholate or sodium dodecyl sulfate, then removing nucleic acid components by eluting with DNase and RNase to yield a third process source tissue;
   freeze drying the third process source tissue to obtain freeze dried tissue and grinding the freeze dried tissue into powder, and dissolving the powder in acid and stirring to obtain the uniform extracellular matrix solution with a mass/volume fraction ranging from 0.1% to 95%;
   step 2: constructing of a synthetic polymer fiber skeleton by processing a synthetic polymer through melt spinning or wet spinning; and
   step 3: preparing the composite tubular material from the uniform extracellular matrix solution and the synthetic polymer fiber skeleton through compounding, comprising soaking the synthetic polymer fiber skeleton in the uniform extracellular matrix solution to obtain a combination of the synthetic polymer fiber skeleton and the uniform extracellular matrix solution;
   freeze-drying or repeatedly air-drying the combination to obtain a tubular material, wherein the tubular material comprises the synthetic polymer fiber skeleton comprising fiber pores filled with an extracellular matrix of the uniform extracellular matrix solution; and
   cross-linking the tubular material with a cross-linking agent, wherein the cross-linking comprises regulating the concentration of the cross-linking agent, regulating cross-linking time to complete the cross-linking, and regulating the pH of the crosslinking reaction in a range of 6 to 8,
   to obtain the composite tubular material;
   wherein the composite tubular material comprises different compounding ratios of the extracellular matrix and the synthetic polymer fiber skeleton obtained by regulating the concentration of the uniform extracellular matrix solution and filling time, wherein the filling time is a time period comprising soaking the synthetic polymer fiber skeleton in the uniform extracellular matrix solution and conducting vacuum pumping until there is no bubble in the uniform extracellular matrix solution.

2. The composite tubular material according to claim 1, wherein the synthetic polymer is one or more of a polyglycolic acid, a poly(lactic-co-glycolic acid), polycaprolactone, a polylactic acid, poly(L-lactide-caprolactone), polyurethane, nylon, polyester, acrylic fibers, polyethylene glycol terephthalate, polypropylene, polyethylene, polycarbonate resin, polystyrene, poly(1,4-polyethylene succinate), poly(1,6-hexamethylene diisocyanate), poly(D-lactic acid), polyethylene glycol, polyglycolic acid, polyhydroxyalkanoate, poly(3-hydroxybutyrate), poly(3-hydroxybutyrate-co-3-hydroxyhexanoic acid), poly(3-hydroxybutyrate-co-3-hydroxyvaleric acid), poly(lactic acid-co-glycolide), poly(propylene fumarate) and poly(dihydroxypropyl fumarate).

3. The preparation method of the composite tubular material according to claim 1, wherein constructing the synthetic polymer fiber skeleton in step 2 comprises the following steps:

installing receiving steel bars with different diameters as receivers on a melt spinning apparatus, adding a synthetic polymer to a constant temperature heating cylinder, heating to melt the synthetic polymer, then regulating a polymer fiber diameter, a fiber angle, and a tube wall thickness by adjusting following parameters of a cylinder piston propulsion speed, an air pressure, a distance between a needle and the receiving bars, a needle thickness, a revolving speed and a lateral movement speed of the receiving bars and fiber receiving time, to prepare the synthetic polymer fibrous skeleton with a fiber diameter ranging from 1 μm to 1000 μm, a fiber angle ranging from 0° to 180°, and a tube wall thickness ranging from 1 μm to 3000 μm.

4. The preparation method of the composite tubular material according to claim 1, wherein the method of constructing the synthetic polymer fiber skeleton through wet spinning in step 2 comprises the following steps:

installing steel bars with different diameters as receivers on a wet spinning apparatus, dissolving a synthetic polymer in a chemically pure reagent to prepare a solution with a mass/volume fraction ranging from 0.1% to 60%, thus yielding a dissolved solution, filling the dissolved solution into a syringe, installing the syringe on a syringe pump, regulating a fiber diameter, a fiber angle and a tube wall thickness by regulating following parameters of a syringe pump propulsion speed, a needle thickness, a revolving speed and a movement speed of the receiving bars, and fiber receiving time, to prepare the synthetic polymer fiber skeleton with a fiber diameter ranging from 1 μm to 1000 μm, a fiber angle ranging from 0° to 180°, and a wall thickness ranging from 1 μm to 3000 μm.

5. The preparation method of the composite tubular material according to claim 1, wherein the cross-linking agent in step 2 comprises one of glutaraldehyde, formaldehyde, a combination of EDC and NHS, genipin and quercetin, wherein EDC and NHS stand for the following: EDC:1-(3-Dimethylaminopropyl)-3-ethylcarbodiimide; and NHS: N-Hydroxysuccinimide.

6. The preparation method of the composite tubular material according to claim 1, wherein a concentration of the uniform extracellular matrix solution ranges from 0.1% to 95% (mass/volume), and the filling time ranges from 0.1 hours to 72 hours.

7. The preparation method of the composite tubular material according to claim 3, wherein the parameter of the constant temperature heating cylinder is set to range from 40° C. to 400° C.

8. The preparation method of the composite tubular material according to claim 5, wherein the parameter of the syringe pump is set to range from 0.1 ml/h to 100 ml/h.

9. The preparation method of the composite tubular material according to claim 4, wherein the chemically pure reagent comprises one of dichloromethane, trichloromethane, an acetic acid, acetone, trifluoroethanol and hexafluoroisopropanol.

* * * * *